United States Patent [19]

Ulrich

[11] 4,319,595
[45] Mar. 16, 1982

[54] DENTAL CARE UNIT

[76] Inventor: Rex Ulrich, 478 W. Heyburn, Twin Falls, Id. 83301

[21] Appl. No.: 116,770

[22] Filed: Jan. 30, 1980

[51] Int. Cl.³ .......................................... A61C 15/00
[52] U.S. Cl. ................................ 132/92 R; 132/84 R; 128/62 A; 128/66
[58] Field of Search ................. 132/90; 128/62 A, 66

[56] References Cited

U.S. PATENT DOCUMENTS

| | | | |
|---|---|---|---|
| D. 246,667 | 12/1977 | Mackay | 128/66 |
| 1,482,747 | 2/1924 | Howe | 128/66 |
| 1,848,621 | 3/1932 | Gollwitzer | 128/62 A |
| 1,995,424 | 3/1935 | Guinness | 128/62 A |
| 2,784,722 | 3/1957 | Chamberlin et al. | 132/92 R |
| 3,225,759 | 12/1965 | Drapen et al. | 128/62 A |
| 3,500,824 | 3/1970 | Gilbert | 128/66 |
| 3,593,707 | 7/1971 | Pifer | 128/62 A |
| 3,605,734 | 9/1971 | Igarashi et al. | 128/66 |
| 4,031,908 | 6/1977 | Ting | 132/91 |

*Primary Examiner*—G. E. McNeill
*Attorney, Agent, or Firm*—Shoemaker and Mattare, Ltd.

[57] ABSTRACT

A dental care unit permits a user to care for his gums, teeth and mouth. The unit is easily stored, and can be used in dental care in a wide variety of situations. The unit includes a chuck for holding dental instruments, and the chuck is connected to a water supply. Included with the dental instruments is a dental flosser.

10 Claims, 26 Drawing Figures

DENTAL CARE UNIT

BACKGROUND OF THE INVENTION

The present invention relates in general to dental care, and, more particularly, to an all purpose dental care unit for home use.

Dental care is a major concern to all people, from infancy on. Even before one has his baby teeth, proper gum care is important so those baby teeth come in properly. Proper care of the baby teeth, as well as proper gum care, is also important so those baby teeth remain healthy.

Once the permanent teeth replace the baby teeth, proper dental care is even more important due to the irreplaceability of those permanent teeth.

Finally, proper care of gums and dentures is also important if dental and periodontal disease or the like are to be avoided.

Proper dental care must include proper care given by an individual in addition to the care provided by a doctor.

In spite of the great importance of proper personal dental care, very few devices are available for permitting an individual to properly care for his teeth, gums and mouth. In fact, there are no systems known to the inventor which permit a person to satisfy all the requirements of proper personal dental care.

Toothbrushes, tooth flossers, water jets and the like are all known and have been known for a long time. However, each of these devices satisfies but one or two dental care requirements.

If a person were to assemble all of the individual personal dental care devices together, great expense would result. Furthermore, a great deal of space in such person's bathroom would be occupied by such devices.

Additionally, cleaning of presently known devices is often difficult and time consuming, thereby discouraging the use thereof.

Often, these devices cannot be properly controlled and modified to meet all the dental needs of a family which includes infants having no teeth, people with baby teeth, and those with dentures.

Accordingly, there is need for a personal dental care unit which can be used to satisfy all the dental care requirements for a user from infancy on.

SUMMARY OF THE INVENTION

The device embodying the teachings of the present invention permits proper care of a user's mouth, gums and teeth from infancy on.

The unit is connected to a water supply and has means for applying toothpaste, mouthwash, medicine, or the like into a user's mouth. The unit includes attachments for toothbrushing, gum massaging, plaque cleaning, flossing, and the like.

The unit is easily transported and stored and is easily cleaned. There are several variations of the basic unit, but all units are interchangeable. The unit is thus easily used at home and elsewhere.

OBJECTS OF THE INVENTION

It is a main object of the present invention to permit complete personal dental care from infancy on.

It is another object of the present invention to provide a personal dental care means which is easily stored.

It is yet another object of the present invention to provide a personal dental care means which is easily cleaned.

It is still another object of the present invention to provide a personal dental care means which is adaptable to many situations.

These together with other objects and advantages which will become subsequently apparent reside in the details of construction and operation as more fully hereinafter described and claimed, reference being had to the accompanying drawings forming part hereof, wherein like reference numerals refer to like parts throughout.

DETAILED DESCRIPTION OF THE INVENTION

Figure 1:
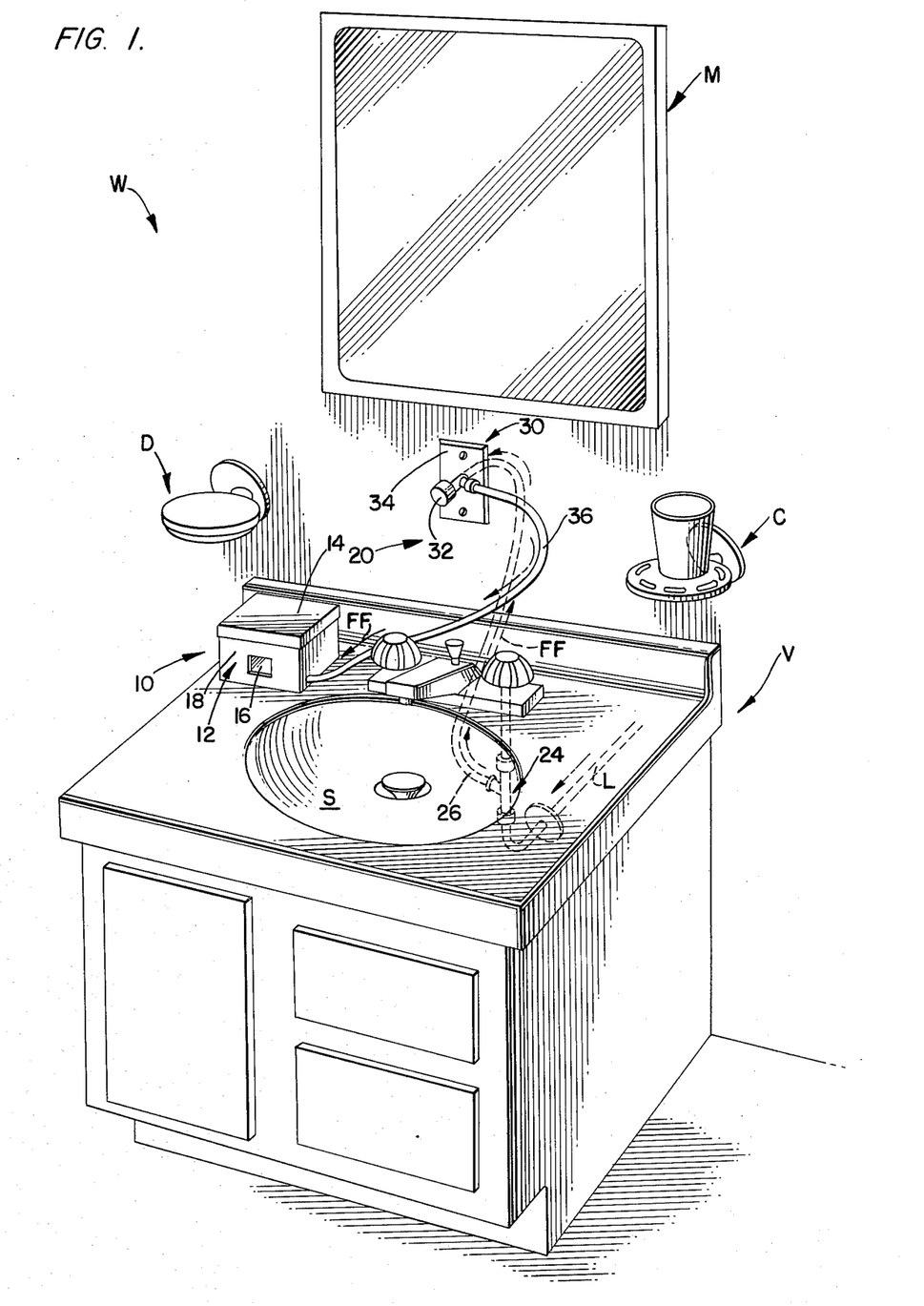
FIG. 1 is a perspective view of a vanity having the dental care unit embodying the teachings of the present invention resting thereon.

Shown in FIG. 1 is a vanity V commonly found in a lavatory, or the like. A mirror M, a soap dish D and a cup holder C are mounted on a wall W adjacent the vanity.

A dental care unit 10 is positioned on the vanity next to sink S thereof. The dental care unit 10 includes a housing 12 having a removable top 14 and a viewing window 16 in one side 18 thereof. A water supply system 20 fluidly attaches the unit 10 to a water supply line L of the lavatory. Preferably, the water supply line L is the cold water supply line. However, if so desired, the system 20 can attach the unit 10 to both the hot and cold water lines. A desired temperature of the fluid supplied to the unit can then by established by proper mixing of the hot and cold water. Alternatively, the unit can be attached only to the hot water supply, if so desired.

Figures 23, 24:
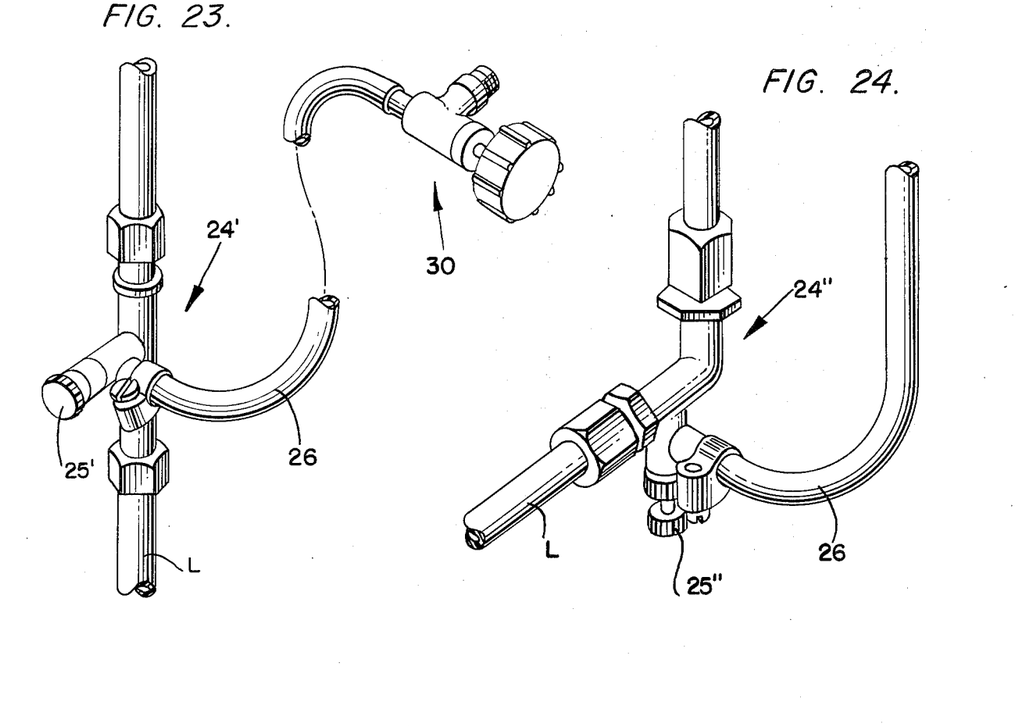
FIGS. 23 and 24 are perspective views of valves which can be used in conjunction with a dental care unit embodying the teachings of the present invention.

The water supply system 20 includes a tee connection 24 fluidly connected to the water supply line L and a flexible hose 26 fluidly attached at one end thereof to the tee connection 24. Two alternative forms of the tee connection are shown in FIGS. 23 and 24, and are denoted by reference indicators 24' and 24", respectively. As shown in FIGS. 23 and 24, the valves 24' and 24" include shutoff valves 25' and 25", respectively, so that the water supply can be controlled downstream of the main valve. The valves 25' and 25" can be any suitable type of valve, such as a ball valve, or the like.

A control valve 30 is mounted on the wall W in a location which is convenient to a user and is fluidly attached to the other end of the flexible hose 26. The valve 30 is preferably a shutoff type valve, and includes a control knob 32 and a wall plate 34. The valve can be a ball valve if so desired.

The flexible hose 36 is fluidly connected at one end thereof to the valve 30 and at the other end thereof to the dental care unit 10. For convenience, the fluid flow direction to the unit 10 is indicated by arrows FF in FIG. 1. Thus, the hose 36 is connected to an inlet end of the valve 30, and the hose 36 is connected to an outlet end of that valve.

Figure 2:
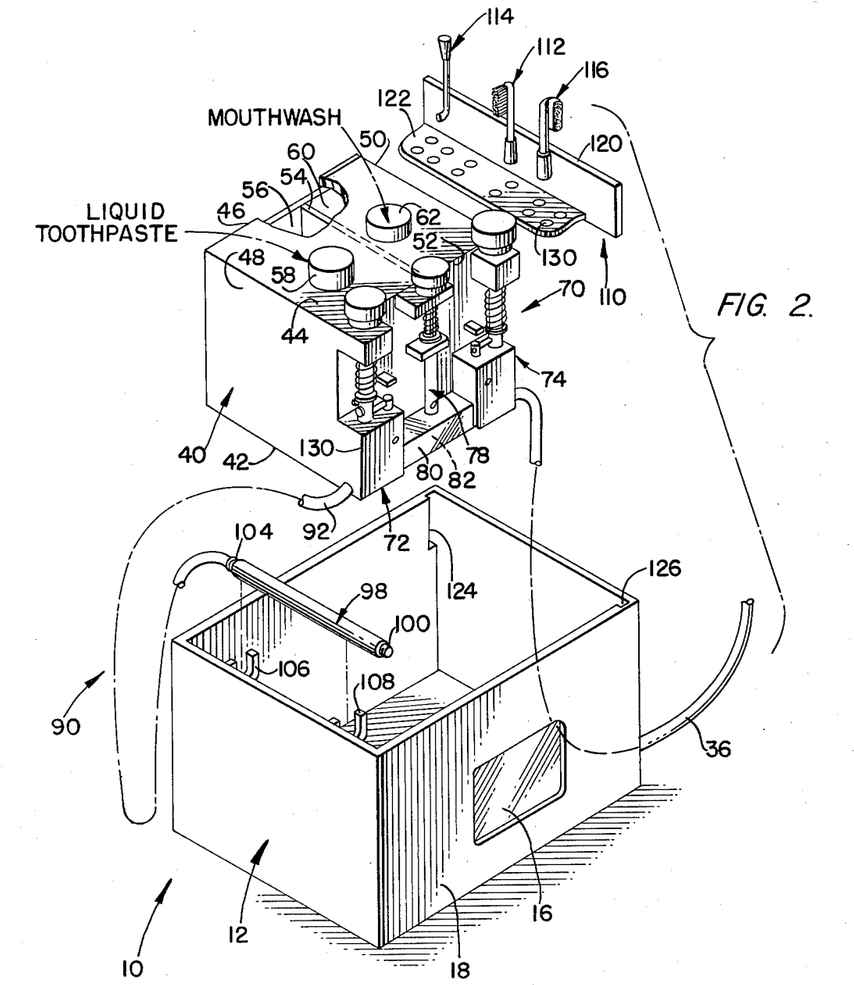
FIG. 2 is an exploded perspective view of a dental care unit embodying the teachings of the present invention.

The dental care unit 10 is best shown in FIG. 2, and includes an internal mounting block 40 releasably received in the housing 12. The block 40 is preferably cubical in shape, but can be other shapes if so desired. The block 40 includes a bottom 42, a top 44, rear wall 46 and side walls 48 and 50, as well as a front wall 52. The block 40 is hollow, and a wall 54 divides that hollow block into a pair of chambers which are located therewithin. As indicated in FIG. 2, one chamber 56 has liquid toothpaste therein, and has a top 58 thereon, and the other chamber 60 has mouthwash therein and a top 62 thereon. The tops 58 and 62 are preferably releasably mounted on the top 44 of the housing to permit refilling the chambers. Thus, screw caps or the like are suitable for use as the tops 58 and 62.

Figure 3:
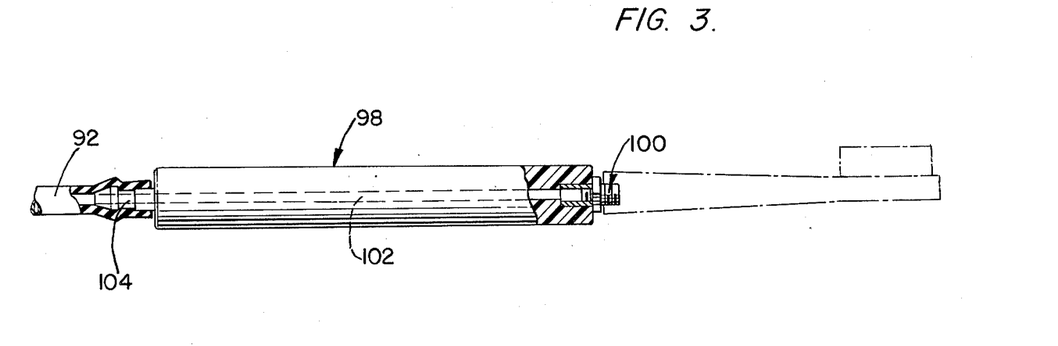
FIG. 3 is an elevation view of a chuck used with the dental care unit embodying the teachings of the present invention.

A dispensing system 70 is mounted on the block front wall 52 and includes toothpaste dispensing control 72 and mouthwash dispensing control 74, as well as a venting mechanism 78. A housing 80 is hollow and has defined therein a central dispensing chamber 82 which is fluidly connected to the venting and control mechanisms which are fluidly connected to the toothpaste and mouthwash containers. As shown in FIGS. 2 and 3, a dental instrument holder 90 includes a flexible hose 92 which is fluidly connected to the central dispensing chamber 82 to receive fluid therefrom. The water supply line 36 is fluidly connected to the chamber 82 at one end of that chamber and the hose 92 is connected to the chamber 82 at the other end of that chamber. The instrument holder includes an elongate hand-held instrument mount 98 attached at one end thereof to the hose 92 to receive fluid therefrom. The mount 98 includes stub 100 on the other end thereof and has a passage 102 defined therethrough to fluidly connect the stub 100 to the hose 92 whereby fluid from the chamber 82 is conducted to a dental instrument mounted on the stub 100. The stub 100 can be brass or other such material. A stub connector 104 fluidly attached hose 92 to the chuck.

As shown in FIG. 2, the instrument mount 98 is mounted on the inside of the housing 12 by brackets 106 and 108. The instrument mount is located within the housing for easy access thereto.

A dental instrument storage rack 110 is mounted on the inside of the housing to store dental instruments in a convenient location. These instruments are preferably suspended from the rack, and include a toothbrush 112, a fluid jet 114, and a gum massager 116 which can be used to apply medicine, salt water or the like to a user's gums. These instruments can include devices used in the care of baby teeth, adult teeth, false teeth, gums and the like. These instruments have threaded bores therein which are used to mount them on the mount 98 via stud 100. The rack is preferably L-shaped with a back 120 and a base 122. The back is mounted in slots 124 and 126 defined in the housing, and the base has instrument mounting means 136 as holes, or the like, defined therein.

Figure 4:
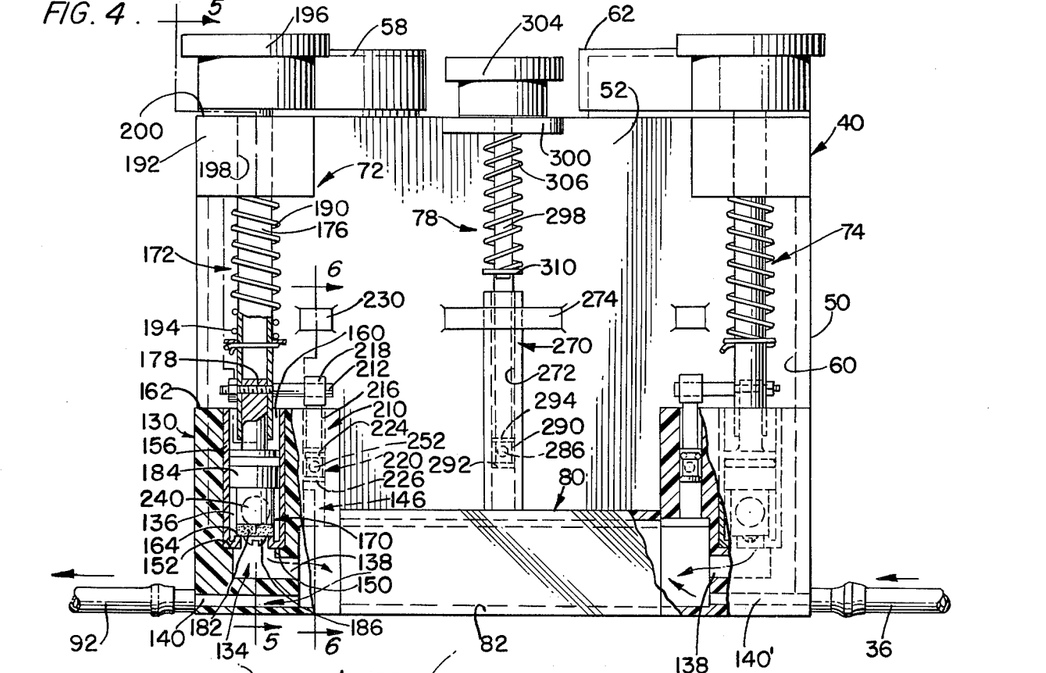
FIG. 4 is a front elevation view of one dental care unit embodying the teachings of the present invention.
Figure 5:
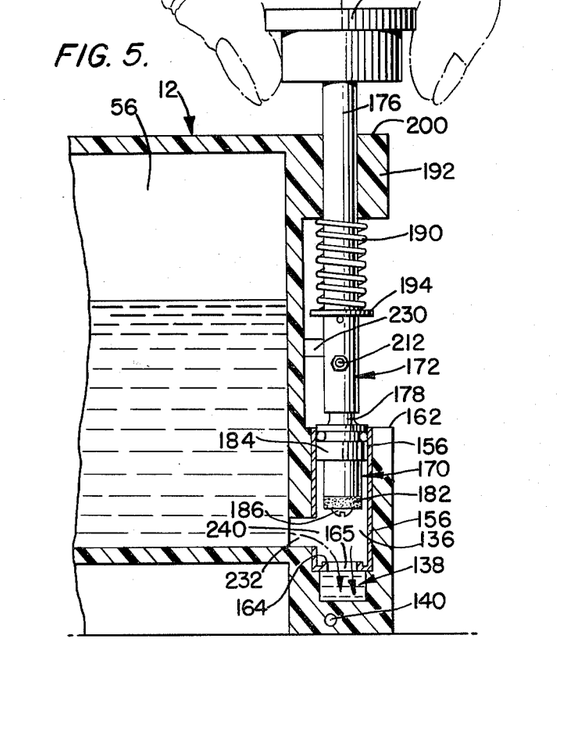
FIG. 5 is a view taken along line 5—5 of FIG. 4.

As shown in FIG. 4, the dispensing controls 72 and 74 are identical, and thus, the following description will relate only to control 72; however, it applies to both controls. The control 72 includes a base housing 130 mounted on front wall 52 of the mounting block 40. The housing 130 has a fluid passage 134 defined therein which has a first, upright portion 136 and a second, horizontal portion 138 fluidly connected to the chamber 82. A dispensing passage 140 is defined in the housing 130 to fluidly connect the chamber with the hose 92. A vent passage 146 fluidly connects the chamber 82 with atmosphere. As shown in FIG. 4, an overhang 150 is located at the juncture of the passages 136 and 138, and defines a portion of a shoulder 152 which surrounds that juncture. A tubular passage liner 156 is positioned within the passage 136, and has an open end 160 coincident with the open end of the passage defined in the top 162 of the housing. The liner is preferably brass, and includes an annular shoulder 164 which defines a valve seat which serves a purpose which will be explained below. A port 165 is defined by the annular shoulder 164 and fluidly connects the passages 136 and 138 as best shown in FIG. 5.

A piston 170 is mounted on a piston rod 172 which includes a tubular shaft 176 and a stub shaft 178 telescopingly received therein. The shafts are preferably plastic. The piston 170 includes sealing means 182 and 184 which are movably and sealingly received in the bore of the liner 156. The sealing means 182 includes a washer mounted on the end of the piston by a fastener such as a brass screw 186, or the like, and the sealing means 184 is spaced from the washer 182 longitudinally of the piston.

A helical spring 190 surrounds the piston rod and on one end thereof abuts a housing 192, and on the other end thereof abuts a spring retainer 194. The housing 192 is mounted on the wall 52, and the spring retainer is mounted on the piston rod. A knob 196 is attached to the end of the piston rod which is remote from the piston. The piston rod is movably received through a passage 198 defined through the housing 192, and the knob abuts the top surface 200 of that housing. The spring preferably biases the piston rod toward a position wherein the washer 182 is seated on the valve seat 164, that is, the FIG. 4 position.

A vent control piston 210 is attached to the piston rod 172 and includes a stub shaft 212 attached at one end thereof to the piston rod and extending horizontally in the direction of the passage 138 toward wall 50 of the base 40. A piston rod 216 is attached to the shaft 212 by a coupling 218 and extends vertically downward from the stub shaft and into the bore 146. A piston 220 similar to piston 170 is mounted on the piston rod remote from the couping 218. The piston 220 includes sealing means 224 and 226, with means 224 including an O-ring, and means 226 including a washer attached to the end of the piston rod. The sealing means 224 and 226 are spaced apart from each other longitudinally of the piston rod.

A stop 230 is mounted on the wall 52 to be abutted by the top of the coupling 218 when a desired amount of travel has been completed by the pistons 170 and 220. Contact between the coupling 218 and the stop 230 stops further upward movement of both pistons 170 and 220 as the coupling 218 is attached to the piston rod 176 via stub shaft 212.

The chamber 56 is fluidly attached to the passageway 136 by a passage 232 which ends in the passage 136 and defines a port 240. In the FIG. 4 position of the piston 170, fluid communication between the port 240 and the chamber 82 is prevented by the washer 182 which is fluidly interposed therebetween. Upward movement of the piston moves the washer above the port 240 and allows fluid from the chamber 56 to flow into the chamber 82 via passage 232, port 240 and passage 134 under the influence of hydrostatic pressure produced by the liquid in the chamber 56 as shown in FIG. 5.

The passage 146 includes a horizontal leg 248 and a vertical leg 250 fluidly connected together by a port 252 which, in the FIG. 4 position of the piston, is located between the seals 224 and 226. The above-discussed upward movement of the piston 170 causes similar upward movement of the piston 220 to a position where fluid communication between chamber 82 and the vent passage is permitted via port 252, thereby venting the chamber to permit free flow of fluid thereinto from the passage 134.

Figure 6:
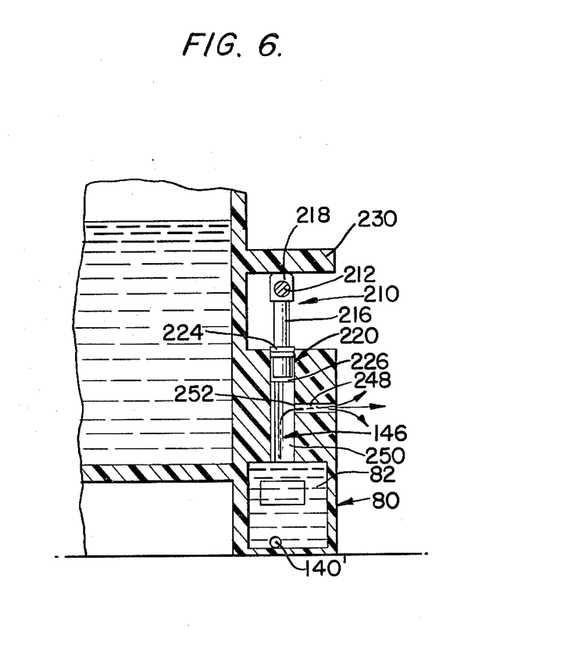
FIG. 6 is a view taken along line 6—6 of FIG. 4.

The up position of the pistons is shown in FIGS. 5 and 6. Upward movement of the pistons is produced by grasping the knob 196 and lifting. Upon release of that knob, the spring 190 returns the pistons to the FIG. 4 closed position.

The venting mechanism 78 includes a tubular housing 270 mounted on wall 52 to essentially upright. The housing 270 includes a bore 272 defined longitudinally thereof and which is fluidly connected at one end thereof to the chamber 82. A bracket 274 is mounted on the wall 52 and supports the housing 270 which is also mounted on the container housing 80.

The chamber 82 is fluidly connected with the bore 272 via a port 286.

A piston 290 is movably mounted within the bore 272 and includes sealing means 292 and 294 which are spaced apart. The piston is mounted on a piston rod 298 which is upright and which is received in the bore 272. The piston rod extends upwardly and is supported by a bracket 300 mounted at or near the top of the wall 52. A knob 304 is mounted on the piston rod at the end thereof which is remote from the piston 290. A helical spring 306 surrounds the piston rod and has the upper end thereof in abutting contact with the bracket 300 and the lower end thereof in abutting contact with the spring retainer 310 mounted on the piston rod 298.

The piston 290 prevents fluid communication between the chamber 82 and the atmosphere in the FIG. 4 position. Upward movement of the piston is effected by lifting the knob 304 upwardly, and this movement is continued until the sealing means 292 is above the port 286, thereby permitting fluid communication between the chamber 82 and atmosphere via the passage 282, the port 286 and the passage 284. The spring 306 returns the piston to the FIG. 4 sealing position upon release of the knob 304. The piston rod is long enough so that the piston cannot be pulled out of the bore 272 by movement of the knob 304.

To operate the unit 10, a user need only charge the chamber 82 with either toothpaste or mouthwash using the control mechanisms 72 or 74 after venting that chamber using mechanism 78.

The valve 30 is then operated to ingest water into the chamber via water line 36 and passage 140' of the control mechanism 74. The water mixes with the fluid in the chamber, and eventually moves a diluted form of that fluid out of the chamber 82 via passage 140 into the hose 92. In the case of liquid toothpaste, the diluted fluid will permit a simultaneous brushing and flushing operation.

The diluted fluid passes through the hose 92 and into the instrument holder 98. A suitable dental instrument is attached to the holder 98 by the stud 100, and the diluted fluid passes out of that dental instrument for use in the dental care operation desired. A dental instrument is not necessary for rinsing with pure water via holder 98 or for injecting mouthwash into a user's mouth. However, instruments can be used for such operations if so desired. Those skilled in the art will be able to envision various instruments and dental operations based on this disclosure, and thus for the sake of brevity, and not for the sake of limitation, further dental operations will not be discussed.

The amount of dental fluid in the chamber 82 is periodically checked using the viewing window 16, and more dental fluid is injected into the chamber 82 as needed during the operation.

Once the operation is completed, the system is flushed using fresh water from the hose 36, and then the system is shut down using the valve 30, or 25', or 25". The flushing step can also be used to inject more, pure water into a user's mouth if so desired. The dental instrument holder 98 is returned to the brackets 106 and 108 after the dental instrument is removed therefrom. An instrument is replaced in the rack 110 and the mounting block 40 is returned to the housing 12. The top 14 is replaced, and the dental unit 10 is thus in a clean, sanitary, out-of-the-way storage condition, and is in a convenient location for further use.

Figure 7:
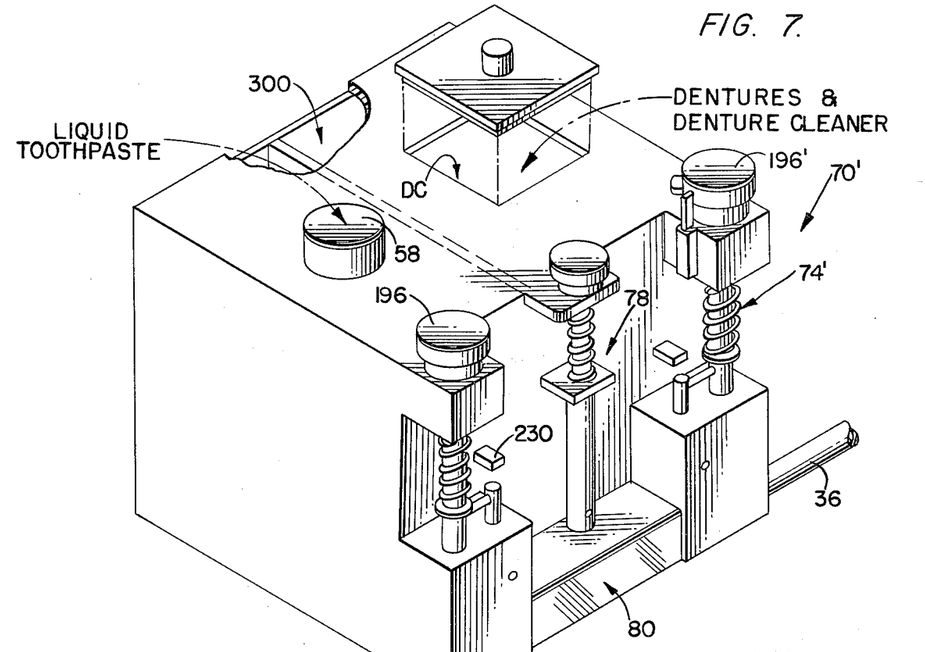
FIG. 7 is a perspective view of another embodiment of the dental care unit embodying the teachings of the present invention.
Figure 8:
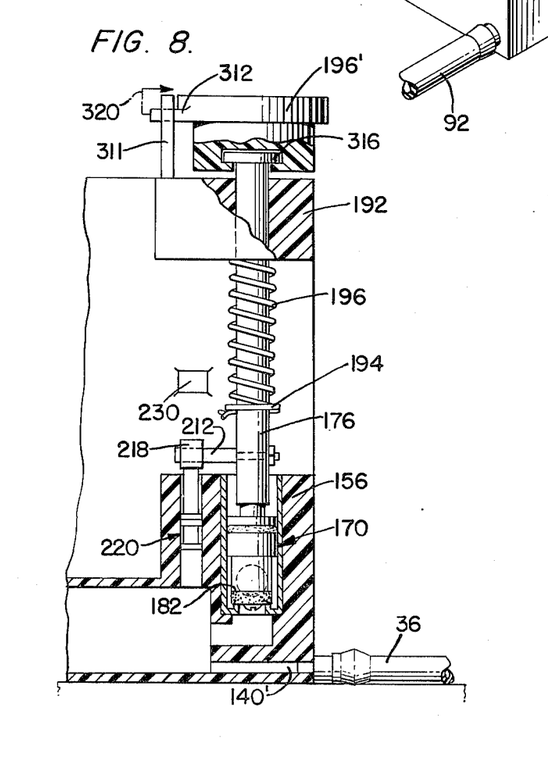
FIG. 8 is a partially cut away elevation view of the FIG. 7 dental care unit in a closed position.
Figure 9:
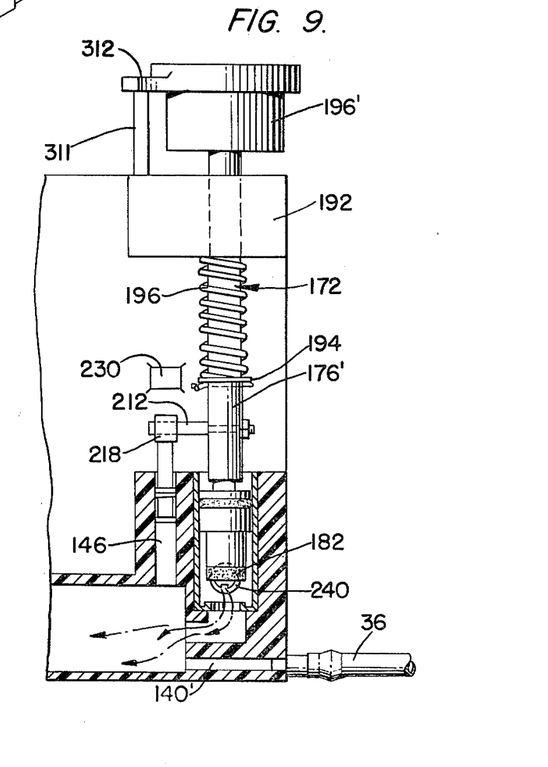
FIG. 9 is a partially cut away elevation view of the FIG. 7 dental care unit in an open configuration.

Shown in FIGS. 7-9 is a unit 10' which is useful for people who have dentures. The unit 10' is similar to the unit 10, and attaches to a cold water supply line as shown in FIG. 1. The unit 10' includes a complete set of water jets, toothbrushes of various angles and straight toothbrushes, and the like. Furthermore, the unit 10' includes a compartment DC in which dentures can be soaked or washed.

The unit 10' includes a dispensing and controlling system 70' which is similar to the system 70 of the unit 10, and the control mechanism 74' is used to dispense denture cleaner into the container chamber 82 to be used in brushing or rinsing dentures. The chamber DC can also be filled with mouthwash and the mechanism 74' used in a manner similar to the mechanism 74.

Medicine can also be placed in the chambers 60 and/or DC to be applied to gums or the like. The unit 10' can be used with or in place of unit 10 as all of the parts of all of the units disclosed herein are interchangeable.

As shown in FIGS. 8 and 9, the unit 10' includes a support 311 on the housing 192 of the mechanism 74' which engages a tab 312 on the knob 196' to support the piston in the open position. This support is used to hold the mechanism open until all the denture cleaning solution is out of the chamber DC and the chamber 82. The knob 196' is rotatably held on the piston rod 176' by a flange 316 so that the piston rod can be moved upwardly, then the knob rotated to engage the tap on the support 311. The just-described movement is indicated by arrow 320 in FIG. 8.

Figures 10, 11:
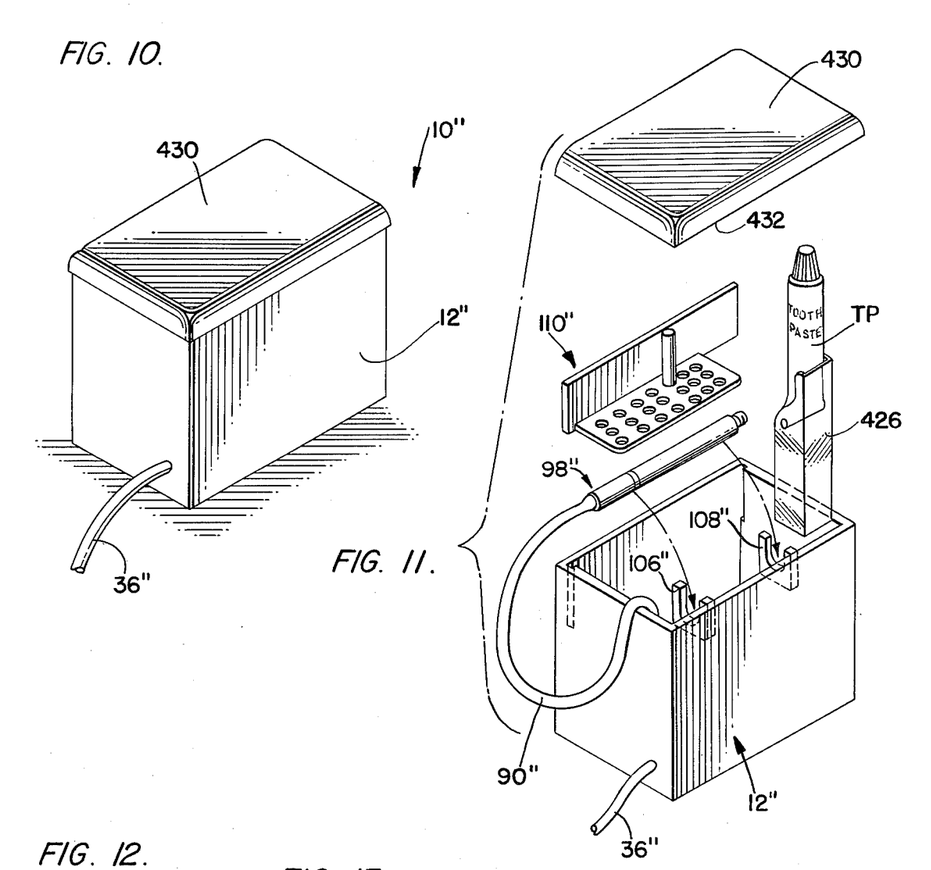
FIG. 10 is a perspective view of another embodiment of the dental care unit embodying the teachings of the present invention.
FIG. 11 is an exploded perspective of the FIG. 10 dental care unit.
Figure 12:
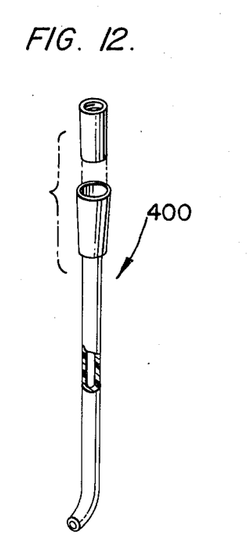
FIGS. 12–15 are perspective views of dental instruments which can be used with any of the dental care units embodying the teachings of the present invention.
Figure 13:
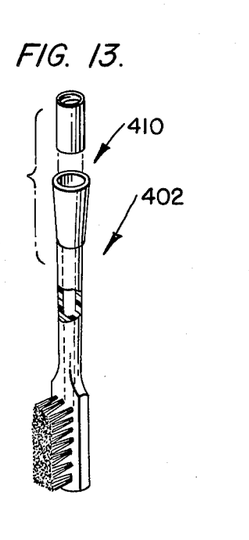
Figure 14:
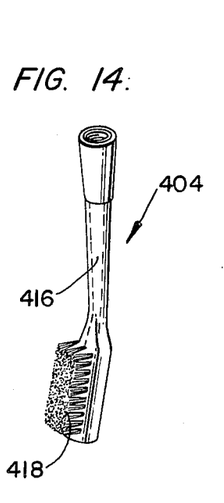
Figure 15:
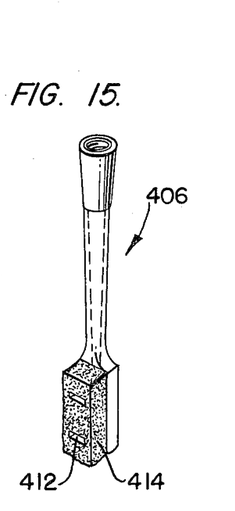

Shown in FIGS. 10 and 11 is a unit 10'' which includes a housing 12'' having a dental instrument rack 110'' releasably mounted therein for holding dental instruments such as a water jet 400 shown in FIG. 12, a straight toothbrush 402 shown in FIG. 13, an angled toothbrush 404 shown in FIG. 14 and/or a gum massager 406 shown in FIG. 15. Each instrument includes an adaptor coupling 410 for attaching that instrument to the chuck or holder 98''. The gum massager includes a plurality of fluid passages each connected to one of the fluid outlets 412 defined in the material 414. The gum massager can also be angled if so desired. Brass inserts can be used in conjunction with the adaptor 410 if so desired. The water jet can be double angled into an angled J configuration if so desired. The angled brush can also be used as a denture brush. The fluid passage 416 is branched, in a U-configuration or the like, beneath the bristles 418 and fluid passages extend from the branches to the base of the bristles to conduct fluid through those bristles. The straight brush can also include a branched fluid passage if so desired.

The holder 98 is attached directly to a water source via lines 90'' and 36'' which are directly connected together in the unit 10''. The holder is mounted on brackets 106'' and 108'' located within the housing 12''. A toothpaste tube holder 426 is mounted in the housing 12'' to releasably store toothpaste TP within the housing.

The unit 10'' includes an adaptor similar to the valve 24 which is located beneath a sink, that is, within the vanity V, that connects to the cold water supply line. The adaptor has a right angle so that the supply line can be broken and then connected to the adaptor. The adaptor includes a valve to regulate flow to the unit 10''. A further valve, similar to valve 30, is connected to the adaptor via suitable lines to further regulate flow to the unit 10''. The line leading from the just-mentioned further valve is connected directly to the chuck 98''.

Lid 430 of the housing includes a chamfer or channel defined on the inner surface of the edges 432 to provide a secure fit between that lid and the housing 12''.

Figure 16:
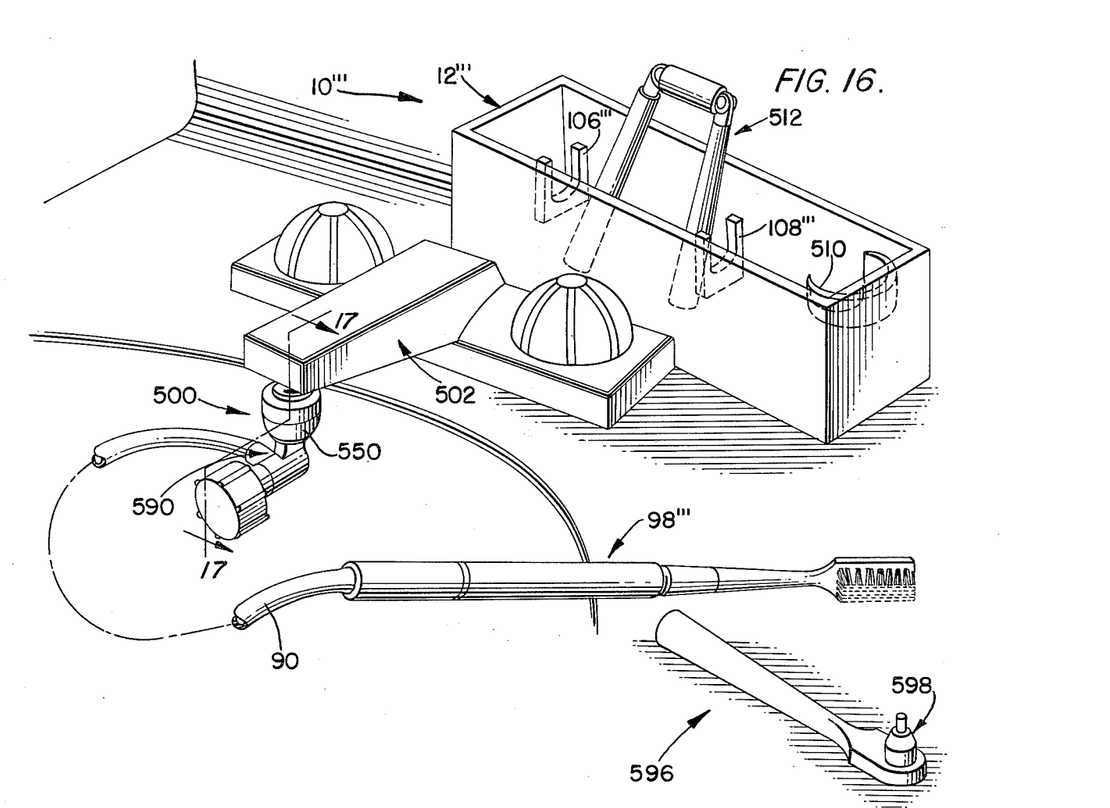
FIG. 16 is a perspective view of yet another dental care unit embodying the teachings of the present invention.
Figure 17:
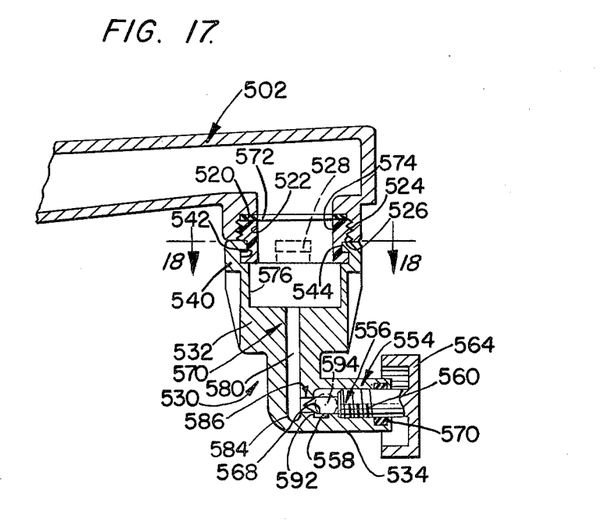
FIG. 17 is a view taken along line 17—17 of FIG. 16.
Figure 18:
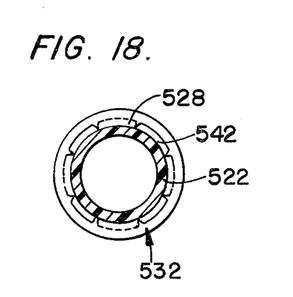
FIG. 18 is a view taken along line 18—18 of FIG. 17.
Figure 19:
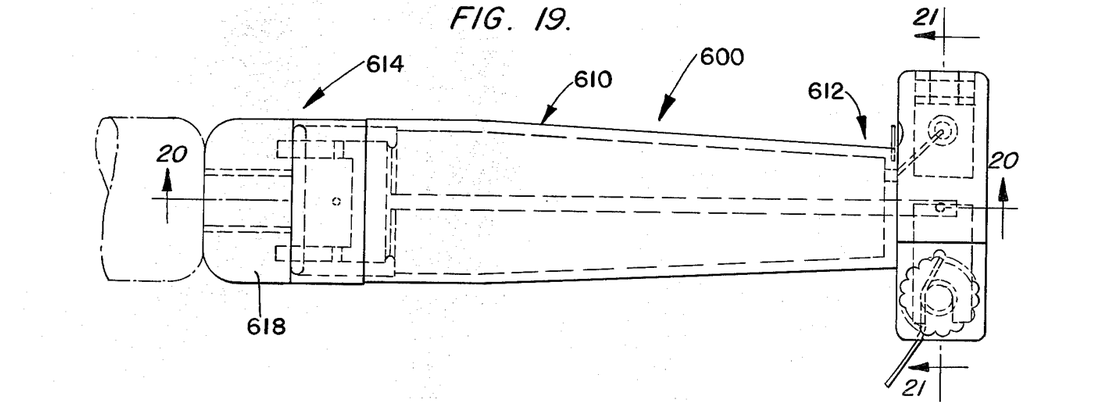
FIG. 19 is a top plan view of a dental flosser used in conjunction with any of the dental care units embodying the teachings of the present invention.

Shown in FIGS. 16, 17 and 18 is a portable unit 10''' which has a special adaptor 500 which fits onto a faucet 502 and includes various adaptors to fit any presently manufactured bathroom faucet. The unit 10''' includes a housing 12''' having brackets 106''' and 108''' for mounting chuck 98''' therewithin. A bracket 510 mounts the adaptor 500 within the housing, and a special wrench 512 is included for removing any couplings present on the faucet 502 prior to installing the adaptor 500. The wrench can be used to install the adaptor onto the faucet also.

The adaptor 500 is shown to include an annular washer 520 which fits within the faucet, and threaded annular coupling 522 having external threads 524 thereon adapted to mate with the threads 526 of the faucet and which has a plurality of lugs 528 on the external surface thereof and which are spaced at approximately equal intervals circumferentially about the coupling.

The adaptor 500 includes a valve 530 having an upper housing 532 and a lower leg 534 thereon. The upper housing 532 includes a coupling section 540 having a circumferential channel 542 defined on the inner surface 544 thereof. The channel 542 mates with the adaptor lugs 528 to fasten the valve 530 to the faucet 502. A plurality of flats 550 are defined on the valve upper section subjacent the coupling section to facilitate secure gripping engagement between the wrench 512 and the adaptor valve 530. The lugs 528 and the channel 542 effect a type of bayonet mounting arrangement.

A needle valve 554 is mounted in the valve leg 534 and includes a body 556 located within a bore 558 defined in the leg 534. The body includes external threads 560 which cooperatively engage mating threads defined in the bore 558 to hold the valve 554 in the leg 534. A control knob 564 is on one end of the body, and a needle assembly 568 is on the other end of the body. A sealing washer 570 is also included to preclude leakage around the valve body. Turning the knob 564 advances or withdraws the needle assembly 568 into or out of the bore 558.

A fluid passage 570 is defined within the adaptor 500 and includes port 572 in the washer 520, a bore 574 in the coupling 522 and a bore 576 in the valve upper section 532. A first fluid passageway 580 fluidly connects at one end thereof to the bore 576 and extends toward the leg 534 to a deadend 584. A second fluid passageway 586 is fluidly connected to one end thereof to the first fluid passageway 580 and at the other end thereof to the bore 558 to fluidly connect that bore to the rest of the just-described passage portions.

A second leg 590 is mounted on the leg 534 to extend at essentially right angles thereto, and includes a third fluid passageway 594 fluidly connected at one end thereof to the bore 558 near the passageway 586. The leg 590 connects to the hose 90 to fluidly connect the chuck 98''' to the faucet 502 via the needle assembly 554.

The fluid passage 586 has a smaller internal diameter than does the bore 558 with which it is axially aligned. Therefore, the intersection between the passage 586 and the bore 558 defines a valve seat 592 for the needle assembly. In the closed configuration shown in FIG. 17, the needle assembly occludes the fluid passage thereby preventing water from passing from the faucet 502 to the hose 90. Double control over fluid flow to the chuck 98''' is thus possible using the faucet controls on the knob 564. Mixing of the hot and cold water flowing from the faucet 502 can be used to effect control of the temperature of water flowing into, and from, the chuck 98'''.

A special water jet 596 is shown in FIG. 16 and includes a tip 598 which directs a small jet of water between teeth or to other such precise locations. The jet 596 also includes brass fittings and the like to be coupled to the chuck 98'''. This jet can also be angled if so desired, and can be used with dentures as well. Other toothbrushes, gum massagers, and the like can be used with the unit 10''' as well. The jet 596 can be used to remove plaque from a user's teeth.

Figure 20:
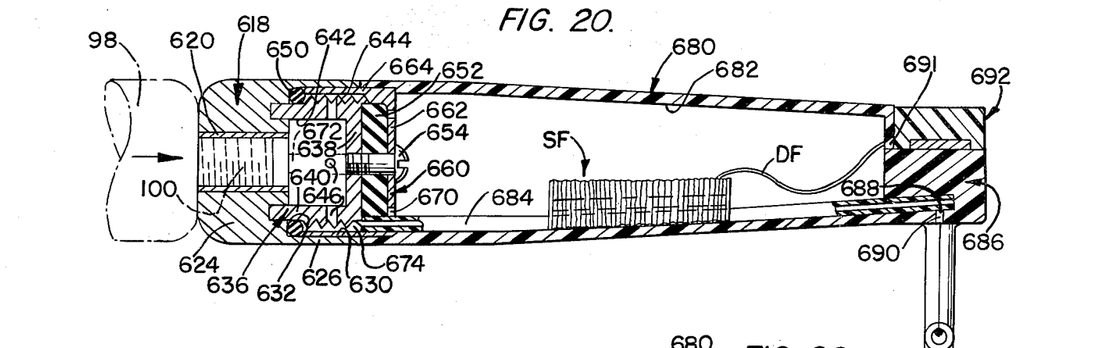
FIG. 20 is a view taken along line 20—20 of FIG. 19.

Shown in FIGS. 19-22 is a floss unit 600 which is an attachment for use with any of the above-described dental care units. The unit 600 attaches to, and makes fluid communication with, the chuck 98 via stud 100. The floss unit includes a body 610 having a distal end 612 and a proximal end 614. As shown in FIG. 20, the proximal end includes a cap 618 having an insert 620, which is preferably brass, threadably attached to the stud 100. The cap includes a base 624 and a skirt 626 extending forwardly of the base. The skirt defines a bore 630 which is axially aligned with the bore of the liner 620. An annular channel 632 is defined in the front surface of the base 624 to surround the liner receiving bore of the cap.

A coupling 636 is cup-shaped and has a base 638 and a wall 640 defining a bore 642. Threads 644 are defined on the external surface of the wall 640, and the wall is snugly received in the channel 632 to mount the coupling 636.

A plurality of radially outward directed fluid passages 646 are defined in the wall 640. Preferably, there are four equispaced fluid passages.

An O-ring seal 650 surrounds the wall 640, and a washer 652 is connected to the coupling base by a fastener, such as a screw 654, or the like.

A cap 660 includes a base 662 and a wall 664 which has internal threads 666 thereon. The threads 666 mate with the threads 644 of the coupling 640 to attach the cap 660 to the coupling 640. A plurality of passages 670 are defined in the cap base 662, and there are a plurality of flats 672 extending longitudinally of the cap. These flats do not have any threads, and thus define a fluid passage 674 with the coupling. The flats are located to intersect the passages 646, and thus, there are preferably four flats. The flats are located to intersect the passages 670 to provide a fluid path between the exterior of the cap 660 and the bore 642, and hence with the chuck 98 and the dental care unit to which the chuck is attached.

A hollow tubular body element 680 is friction fit onto the cap 660 and has a bore 682 defined longitudinally therethrough.

A flow tube 684 is mounted within the bore 682 and has one end received in one of the passages 670 to be in fluid communication with the fluid passage 674 to receive fluid therefrom. The other end of the tube 684 is fixed in front cap 686 of the body portion. It is noted that the cap closes the fluid passages defined by the flats, and thus fluid can pass only through the fluid passage which is connected to the flow tube 684.

The tube has a port 688 defined therein near one end thereof, and the front cap closes the end of the tube so that fluid flowing through the tube will pass through the port 688. The cap 688 has a fluid passage 690 defined therein to receive fluid from the port 688 and conduct such fluid outwardly thereof as shown in FIG. 21 by arrow CF.

A spool SF of dental floss DF is mounted in the bore 682. The dental floss is fed from the spool through a floss passage 691 defined in the front of the body 680.

A floss head 692 is mounted on the front cap 686, and includes a housing 694 having a top 696, front face 698, rear face 700, end faces 702 and 704, and bottom face 706. The head 692 further includes a top cap 708 hingeably connected to the housing 694 by a hinge 710 and pintle 712 adjacent end face 704 to open in the direction indicated by arrow TO in FIG. 21. A pair of hollow, L-shaped prongs 716 and 718 are attached to housing bottom face 706 to depend therefrom. Each prong has an L-shaped bore 720 and 721, respectively, defined therethrough.

Figure 21:
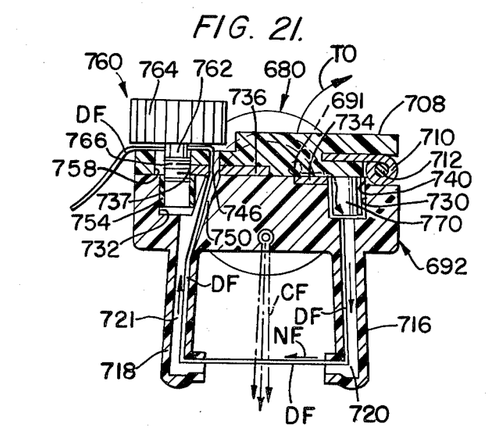
FIG. 21 is a view taken along line 21—21 of FIG. 19.

A pair of bores 730 and 732 are defined in the housing 694 to be axially aligned with the prong bores 720 and 721 as best shown in FIG. 21. A plate 734 is mounted on the housing to be located superjacent bore 730 and a plate 736 is also mounted on the housing to be located superjacent bore 732. The plate 734 has a hole 740 defined therethrough to be aligned with the bore 730. The plate 736 has an end edge 737 located adjacent the bore 732 and is either shaped, or has screw threads defined on that end for a purpose to be discussed below. The plate 736 also includes a further hole 746 defined therethrough adjacent the just-mentioned end thereof as best shown in FIG. 21. The hole 746 is aligned with a hole 748 defined in the housing 694 which is the intersection between the housing top 696 and a bore 750 defined in the housing. The bore 750 has one end intersecting the top 696 and the other end intersecting bore 721 of the prong 718. Preferably, the bore 750 is slightly angled with respect to bores 721 and 732.

A liner 754, which is preferably brass, is located within the bore 732. The liner can have screw threads defined internally thereof, if so desired.

The top cap 708 has a hole 758 defined therethrough to be aligned with the bore 732, and a top cap hold-down means 760 is received through the hole 758. The hold-down means includes a threaded shaft 762 attached at one end thereof to a knob 764 and having screw threads 766 on the shaft thereof. The screw threads 766 cooperatively engage the end 737 of the plate 736 to threadably attach the hold-down means to the plate 736, and hence to the housing 694. As shown in FIG. 21, the knob 764 abuts top surface 768 of the top cap at the end thereof which is located remote from the pintle 712 to hold the top cap in the FIG. 21 closed position. A peg 770 is attached at one end thereof to the top cap and is located and sized to fit snugly within the bore 730 as shown in FIG. 21 when the top cap is held down by the hold-down means 760.

Figure 22:
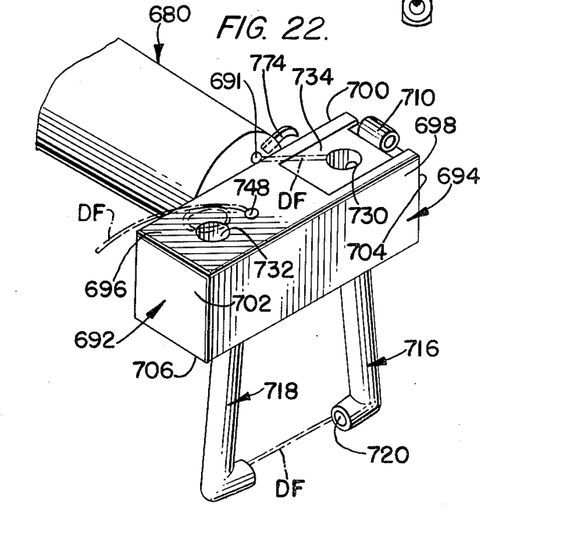
FIG. 22 is a perspective view of the fore portion of the FIG. 19 dental flosser.

As shown in FIGS. 21 and 22, the dental floss DF passes through hole 691 in the body 680, then into the bore 730, and into the passage 720 of the prong 716. The floss then spans the space between the prongs, enters the passage 721 of the prong 718 and the bore 750. The floss then passes through the hole 746 in the plate 736 and is wrapped around the shaft 762 as indicated in FIG. 22. When the top cap 708 is held in place by the hold-down means, the peg 770 and the shaft 762 of the hold-down means securely hold the floss in place, and that floss can be stretched tightly across the area between the two prongs 716 and 718.

The floss instrument can be inserted into a user's mouth for a flossing operation while that instrument is fluidly connected to a dental care unit so that fluid, such as medicine, mouthwash, water, or the like, can be directed into that user's mouth during the flossing operation.

When a new length of floss is desired, the top cap is lifted in the direction of arrow TO after the hold-down means 760 is released and the floss is then unwound from the shaft 762. The floss is pulled in the direction of arrow NF in FIG. 21 until the desired amount of floss has been removed from the spool SF. The old floss is cut off using a knife 774 which is mounted on the body front face adjacent the floss passage 691 as shown in FIG. 22. The placement of the knife 774 with respect to the hold-down means 760 permits sufficient floss to remain after cutoff to allow that floss to be secured to the hold-down means as above-described.

The spool SF can be encased in a sheath having a floss hole defined therein to avoid hanging up of the floss.

Figure 25:
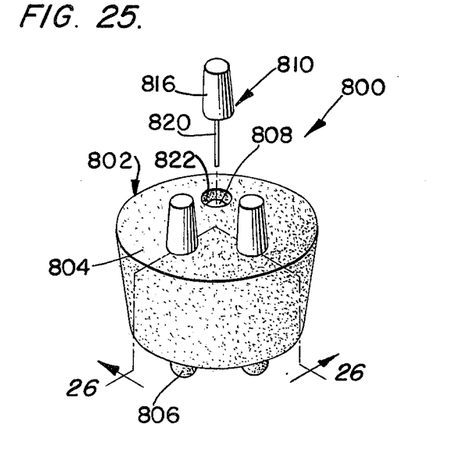
FIG. 25 is a perspective view of a dental instrument cleaner and holder device which can be used with a dental care units embodying the teachings of the present invention.
Figure 26:
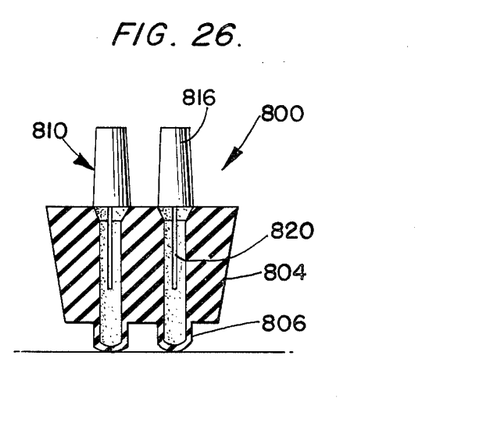
FIG. 26 is a view taken along line 26—26 of FIG. 25.

A device for cleaning the passages of the water jets discussed above is shown in FIGS. 25 and 26 and is indicated by the reference numeral 800. The device 800 includes a base 802 having a body 804 and supports 806. A plurality of bores 808 are defined in the body 804, and cleaners 810 are accommodated within those bores. Each of the cleaners includes a handle 816 and a prong 820. The prongs are sized to fit into the fluid passages of the water jets to ream out those passages to remove any material which may have become lodged therein. The bores include counterbores 822 to securely hold the cleaners 810. The body 804 is preferably rubber, but can be any other suitable material. The cleaning device can be included with any of the above-discussed dental care units.

As this invention may be embodied in several forms without departing from the spirit or essential characteristics thereof, the present embodiment is, therefore, illustrative and not restrictive, since the scope of the invention is defined by the appended claims rather than by the description preceding them, and all changes that fall within the metes and bounds of the claims or that form their functional as well as conjointly cooperative equivalents are, therefore, intended to be embraced by those claims.

I claim:

1. A dental care unit comprising:
   a housing;
   a hollow base accommodated in said housing, said base including a plurality of containers therein for storing a plurality of liquids in said base;
   a plurality of dispenser control mechanisms on said base each being fluidly connected to an associated one of said containers for controlling the amount of liquid removed from said associated container, each control mechanism including a base housing, a fluid passage defined in said base having a first portion and a second portion, a dispensing passage defined in said base, a vent passage defined in said base, a dispensing piston located in said first portion, urging means biasing said dispensing piston into said upright portion, a vent control piston located in said vent passage and coupled to said dispensing piston, a stop mounted to abut said vent control piston to limit the travel of said pistons, seal means on said control mechanism piston, said control mechanism piston being movable from a first position wherein said seal means prevents fluid communication between said associated container and said fluid passage to a second position permitting such fluid communication, and means for moving said control mechanism piston;
   a mixing chamber defining means on said base having a mixture chamber fluidly connected to said dispensing passages of said dispenser control mechanisms to receive liquid therefrom, said mixing chamber defining means including a piston received in a piston bore which is fluidly connected to said mixing chamber and to atmosphere, stop means limiting the amount of movement of said mixing chamber piston, seal means on said piston, said mixing chamber piston being movable to a first position wherein said seal means prevents fluid communication between said mixing chamber and atmosphere to a second position permitting such fluid communication, and means for moving said mixing chamber piston;
   an inlet hose fluidly connected to one dispensing passage of said dispensing passages for conducting liquid thereoutof;
   whereby with said control mechanism pistons and said mixing chamber piston in said second positions fluids from containers associated with said control mechanisms flow from said containers to said mixing chamber and liquid conducted into said one dispensing passage flows into said mixing chamber to mix with said fluids to form a mixture, said mixture flowing out of said mixing chamber and into said outlet hose via said another dispensing passage, said control mechanism venting means controlling fluid flow into said fluid passage first portion and said mixing chamber piston controlling flow into said mixing chamber so that mixing of said fluid and said liquid is controlled;
   a chuck connected to said outlet hose, said chuck having a fluid passage therein which is fluidly connected to said outlet hose; and
   a plurality of different dental care instruments in said housing, each instrument performing a different dental function, and each instrument having means for attaching said each instrument to said chuck, each instrument having a fluid passage therein which is fluidly connected to said chuck fluid passage and liquid dispensing means for dispensing liquid into a user's mouth.

2. The dental care unit defined in claim 1 further including denture care means on said base, said denture care means including a chamber defined in said base.

3. The dental care unit defined in claim 1 further including storage means in said housing for storing said dental care instruments in said housing.

4. The dental care unit defined in claim 1 wherein one of said dental instruments includes a dental flosser, said dental flosser including a cap having means for connecting said cap to said chuck and fluid passage means which is fluidly connected to said chuck fluid passage, a coupling mounted on said cap and having a bore therein which is fluidly connected to said cap fluid passage, said coupling including a plurality of fluid passages fluidly connected to said coupling bore and a plurality of thread segments which are interrupted adjacent said coupling fluid passages, a second cap connected to said coupling and having threads for engaging said coupling threads, the areas between said interrupted cooling threads and said second cap defining flow paths which are fluidly connected to said coupling bore via said coupling fluid passages, a tube fluidly connected to one of said flow paths, a hollow body connected to said second cap, dental floss dispensing means connected to said body, dental floss storage means mounted in said hollow body, dental floss holding means mounted on said body, and fluid dispensing means fluidly connected to said tube to dispense fluid adjacent and on dental floss held in said dental floss holding means.

5. The dental care unit defined in claim 1 further including a dental instrument cleaning means associated with said housing, said cleaning means including a base, a plurality of bores defined in said base, and a plurality of cleaners in said bores, each of said cleaners including a handle and a prong.

6. The dental care unit defined in claim 4 wherein said dental floss holding means includes a housing, a pair of prongs on said housing, a closure cap movably mounted on said housing, dental floss guide means in said housing and in said prongs, dental floss passage means in said body, and dental floss jamming means on said housing.

7. The dental care unit defined in claim 6 wherein said dental floss jamming means includes a prong on said top cap and a threaded fastener on said top cap.

8. The dental care unit defined in claim 7 wherein said prong extends into one of said dental floss passage means.

9. The dental care unit defined in claim 8 further including a plate on said top cap which has an edge adapted to be threadably attached to said fastener.

10. The dental care unit defined in claim 9 wherein said dental floss storage means includes a spool located in said hollow body.

* * * * *